(12) United States Patent
Schumacher et al.

(10) Patent No.: US 8,292,990 B2
(45) Date of Patent: Oct. 23, 2012

(54) NEBULIZER WASTE PRESSURE REDUCER FOR HPLC SYSTEMS

(75) Inventors: Michael Schumacher, Forest Lake, MN (US); Robert Montividas, Lino Lakes, MN (US)

(73) Assignee: TSI, Incorporated, Shoreview, MN (US)

( * ) Notice: Subject to any disclaimer, the term of this patent is extended or adjusted under 35 U.S.C. 154(b) by 518 days.

(21) Appl. No.: 12/555,493

(22) Filed: Sep. 8, 2009

(65) Prior Publication Data

US 2010/0058840 A1    Mar. 11, 2010

Related U.S. Application Data

(60) Provisional application No. 61/094,618, filed on Sep. 5, 2008.

(51) Int. Cl.
*B01D 19/00* (2006.01)
(52) U.S. Cl. ............ 95/241; 95/266; 96/193; 96/219; 73/61.52
(58) Field of Classification Search .......... 96/193, 96/219; 95/241, 266; 73/61.52
See application file for complete search history.

(56) References Cited

U.S. PATENT DOCUMENTS

| | | | |
|---|---|---|---|
| 5,011,519 A | 4/1991 | Maeda | |
| 5,275,486 A * | 1/1994 | Fissenko | 366/178.3 |
| 6,283,140 B1 | 9/2001 | von Palffy et al. | |
| 6,813,929 B2 | 11/2004 | Jochum, Jr. | |
| 7,208,123 B2 | 4/2007 | Knollenberg et al. | |
| 7,235,214 B2 | 6/2007 | Rodier et al. | |
| 7,256,044 B2 | 8/2007 | Karlsson et al. | |
| 2002/0144949 A1 | 10/2002 | Berger et al. | |
| 2004/0214344 A1 | 10/2004 | Anderson, Jr. et al. | |
| 2005/0103721 A1 | 5/2005 | Fritze | |
| 2006/0219637 A1 | 10/2006 | Killeen et al. | |
| 2007/0072285 A1 | 3/2007 | Barringer, Jr. | |
| 2008/0121576 A1 | 5/2008 | Gerhardt et al. | |
| 2008/0135484 A1 | 6/2008 | Hammer | |
| 2008/0154543 A1 | 6/2008 | Rajagopal et al. | |

FOREIGN PATENT DOCUMENTS

| | | |
|---|---|---|
| WO | WO 2004/111632 | 12/2004 |
| WO | WO 2005/033714 | 4/2005 |
| WO | WO 2008/073361 | 6/2008 |

OTHER PUBLICATIONS

Fox & McDonald, Introduction to Fluid Mechanics, $2^{nd}$. Ed., pp. 368-371 (J. Wiley and Sons, 1978).
Madellan Biosciences, "Corona CAD Technology—How it Works," (Sep. 2009).

(Continued)

*Primary Examiner* — Robert A Hopkins
(74) *Attorney, Agent, or Firm* — Patterson Thuente Christensen Pedersen, P.A.

(57) ABSTRACT

A High Performance Liquid Chromatography (HPLC) system including a pressure reducer assembly for reducing pressurized streams to ambient pressure. The pressure reducer assembly includes first and second flow restrictors, each coupled to a common chamber that acts as a surge suppressor that mitigates pressure spikes in the discharge lines. The flow restrictors may comprise tubes having a high length-to-diameter ratio. The pressure losses through the flow restrictors, in combination with transition losses as the flow stream enters and exits the chamber, are sufficient to reduce a discharge stream from a specified inlet pressure to substantially ambient pressure, thus eliminating the need for pressurized waste containers.

7 Claims, 4 Drawing Sheets

OTHER PUBLICATIONS

OptiCal Sciences, "High Pressure Diffuser," http://www.optical-sciences.co.uk/Products_High_Pressure_Diffuser.asp (2007).
BPA Air Quality Solutions LLC, "High pressure diffuser for use with remote or portable air testing equipment in high pressure applications . . . " Lighthouse High Pressure Diffuser Laser Particle Counter Accessory—BreathePureAir_com.mht (2001).
Emtek, LLC, "EMTEK High Pressue Diffuser," Metek High Pressure Diffuser.mht, (2009).
Pacific Scientific Instruments, "Met One, Isoprobes," (Sep. 2009).

* cited by examiner

NEBULIZER WASTE PRESSURE REDUCER FOR HPLC SYSTEMS

RELATED APPLICATIONS

This application claims the benefit of U.S. Provisional Patent Application No. 61/094,618, filed Sep. 5, 2008, which is hereby incorporated by reference in its entirety herein.

FIELD OF THE INVENTION

The present disclosure relates generally to the field of pressure reducers and more particularly to reducers that reduce the pressure of a mixed gas/liquid stream for containment in a container.

BACKGROUND OF THE INVENTION

Chromatography is a valuable tool for separating, quantifying and identifying chemical compounds. In a High Performance Liquid Chromatography (HPLC) system, a liquid sample containing a target compound is introduced into a column under pressure. The target compound is introduced into a mobile phase, which is contacted with a stationary phase. The speed of travel through the column depends on the mobile phase non-covalent interactions of the target compound with the stationary phase. HPLC systems utilize various detectors capable of generating a signal that varies with the target compound concentration eluting from the separation column. An example of an HPLC detector is the CARONA CAD manufactured by ESA of Chelmsford, Mass., USA. The CARONA CAD includes a nebulizer that receives a solution eluting from a separation column, then atomizes and sprays the solution in an aerosol stream as droplets, which dry to form residue particles. A corona discharge source or needle selectively charges the residue particles as the aerosol stream enters a chamber. The selectively charged residue particles, each carrying a charge in proportion to its size, are collected at a conductive filter. The electrical current along a conductor coupled to the filter is measured to provide an indication of concentrations of the target compound.

The detection process as outlined above results in a waste mixture of gas and liquid exiting the nebulizer. The waste mixture is also well above atmospheric pressure because the system must operate under elevated pressure to atomize and spray the particles. The waste mixture is typically siphoned into sealed bottles ostensibly capable of withstanding pressure that may reach or exceed 3.5-psid.

The pressurized bottles can present myriad problems for running the HPLC system. The waste mixture typically flows from the nebulizer in uneven, alternating plugs of gas and liquid, and can cause pressure spikes that that create noise in the electronic detection signal of the nebulizer and attendant difficulty in accurately assessing the target compound concentration. In addition to the signal noise, the pressurized system can present safety issues. In many applications, the nebulizer waste contains hazardous solvents or particles. While the bottles are ostensibly designed to withstand pressure, the risk of explosion or leak is sufficiently high enough that many facilities cannot use the detection system. The bottle also takes up space which is often at a premium in the laboratory setting, and typically requires special handling disposal techniques that are more costly than simply routing the waste stream to a drain or to a remote container.

It is known that fluid flow through small diameter tubes can create a loss in pressure, as is described in U.S. Pat. No. 6,813,929 assigned to Dionex Corporation. Another potential solution may be to include pumps downstream of the nebulizer similar to those described in US Publication No. 2008/0154543 to Rajagopal. However, the small diameter tubes alone have proven insufficient for completely de-pressurizing a waste system or satisfactorily mitigating noise. Pumps may be effective for reducing pressure but introduce additional costs in equipment and maintenance and may not mitigate the problematic pressure spikes.

Other steps may be taken to reduce the inherent safety risk. For example, the waste bottle may be kept in a cage or similar sealed container. The addition of a cage/container, however, increases the footprint of the system and still may not meet safety codes. Simply minimizing safety risks also does nothing to eliminate noise in the detection signal.

A device that can simply and economically reduce the signal noise caused by pressure spikes and eliminate the need for pressurized waste containers would be welcome.

SUMMARY OF THE INVENTION

Various embodiments of the present invention may be utilized with virtually any system generating a fluid output at an elevated pressure, and de-pressurizing waste fluid mixtures to atmospheric pressure while occupying little space. Accordingly, an HPLC aerosol-based detection system may be utilized in a variety of facilities with diminished or no risk of hazardous waste explosion. An added benefit of reducing fluid pressure in certain embodiments of the present invention is the reduction of signal noise from the pressure spikes of uneven fluid flow.

In one embodiment, an apparatus for reducing the pressure of a fluid flow stream comprises a pressure reducer assembly defining a chamber therein, the pressure reducer assembly also including a first flow restrictor configured to receive the fluid flow stream and to deposit the fluid flow stream into the chamber. A second flow restrictor may also be included, configured to receive the fluid flow stream from the chamber and to convey the fluid flow stream out of the chamber. In this embodiment, each of the first and second flow restrictors define first and second flow axes, respectively, and are tailored to cause a predetermined first and second reduction in pressure, respectively. The pressure reductions may be tailored so that the fluid flow stream exits the second flow restrictor at substantially atmospheric pressure. The first and second flow axes may be in parallel and may be co-linear.

In another embodiment, a method for reducing the pressure in a waste receptacle comprises providing a first flow restrictor in fluid communication with a chamber and a second flow restrictor in fluid communication with the chamber and the waste receptacle. Fluid that is at a first pressure is caused to flow through the first flow restrictor, the first flow restrictor being configured to create a first loss of pressure when the fluid enters the first flow restrictor at the first pressure, wherein the first pressure is greater than atmospheric pressure. The fluid that flows through the first restrictor then flows into the chamber, the chamber operating at a second pressure that is greater than atmospheric pressure and less that the first pressure. The fluid that is at the second pressure flows through the second flow restrictor, the second flow restrictor being configured to create a second loss of pressure when the fluid enters the second flow restrictor at the second pressure. The fluid that flows through the second flow restrictor flows into the waste receptacle, the waste receptacle being substantially at atmospheric pressure.

In one embodiment, a system for reducing the pressure in a waste stream of a High Performance Liquid Chromatography (HPLC) system comprises a nebulizer unit, a filter assembly configured to receive the waste stream from the nebulizer unit, and a pressure reducer assembly including a chamber defined therein and adapted to receive the waste stream from the filter assembly. The pressure reducer assembly of this embodiment includes an inlet tube in fluid communication with the chamber and the filter assembly, the inlet tube having a length and diameter configured to cause a first predetermined reduction in pressure. The pressure reducer assembly of this embodiment also includes an outlet tube in fluid communication with the chamber and which empties into a drain or container. The outlet tube may have a length and diameter configured to cause a second predetermined reduction in pressure. One or both of the inlet and outlet tubes may be oriented substantially vertically in operation. Alternatively or in addition, the inlet and outlet tubes may be substantially parallel and/or co-linear.

DETAILED DESCRIPTION OF THE DRAWINGS

Figure 1:
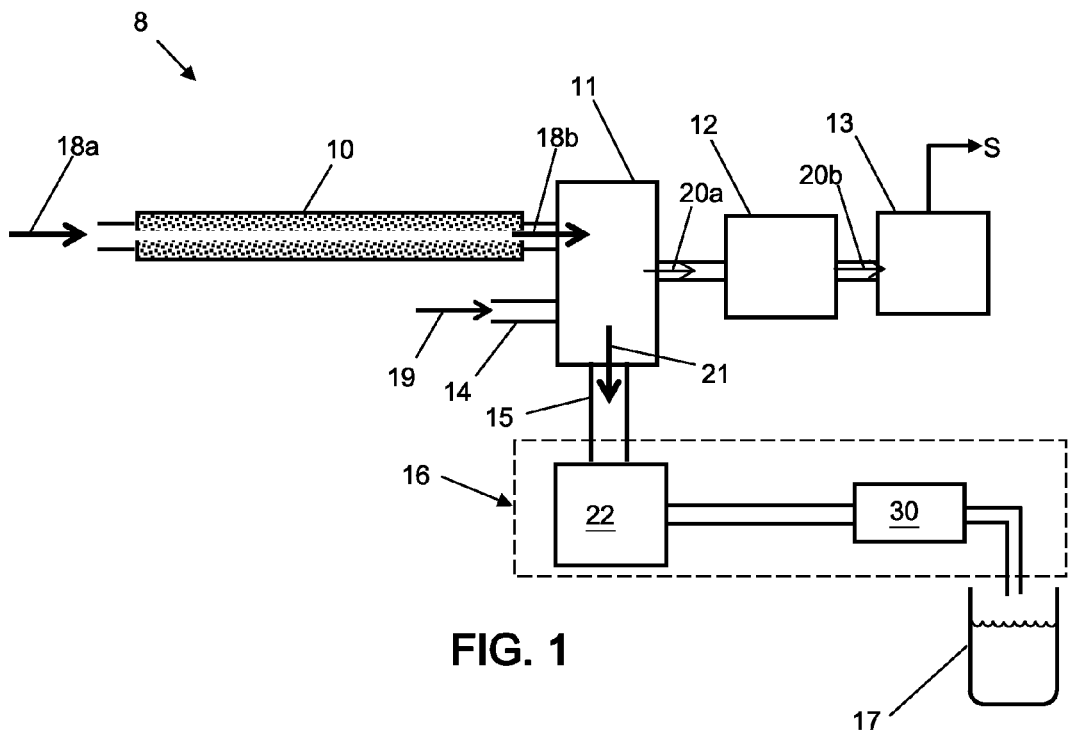
FIG. 1 is a schematic of a high performance liquid column and detection system in an embodiment of the invention.

Referring to FIG. 1, a High Performance Liquid Column (HPLC) system 8 is depicted in an embodiment of the invention. The HPLC system 8 comprises a separating column 10 in fluid communication with a nebulizer 11, a particle charger 12 and a collector 13. The nebulizer 11 of this embodiment includes a gas inlet 14 and a waste outlet 15. The waste outlet 15 is in fluid communication with a waste trap assembly 16, which may deposit the waste stream in a waste container 17.

In operation, a liquid sample 18a is introduced to the stream of mobile phase that enters the separating column 10. An eluant 18b of separated components exit the separating column 10 and enters the nebulizer 11. A pressurized gas 19 enters the gas inlet 14 of the nebulizer 11 for nebulization of the eluant 18b. An aerosol 20a enters the particle charger 12 which charges the aerosol 20a and passes the charged aerosol 20b onto the collector 13. The charged aerosol 20b interacts with the collector 13 to produce a signal S for processing. A portion of the eluant 18b and pressurized gas 19 exits the nebulizer 11 as a waste stream 21 via the waste outlet 15 and is passed on to the waste trap assembly 16.

Figure 2:
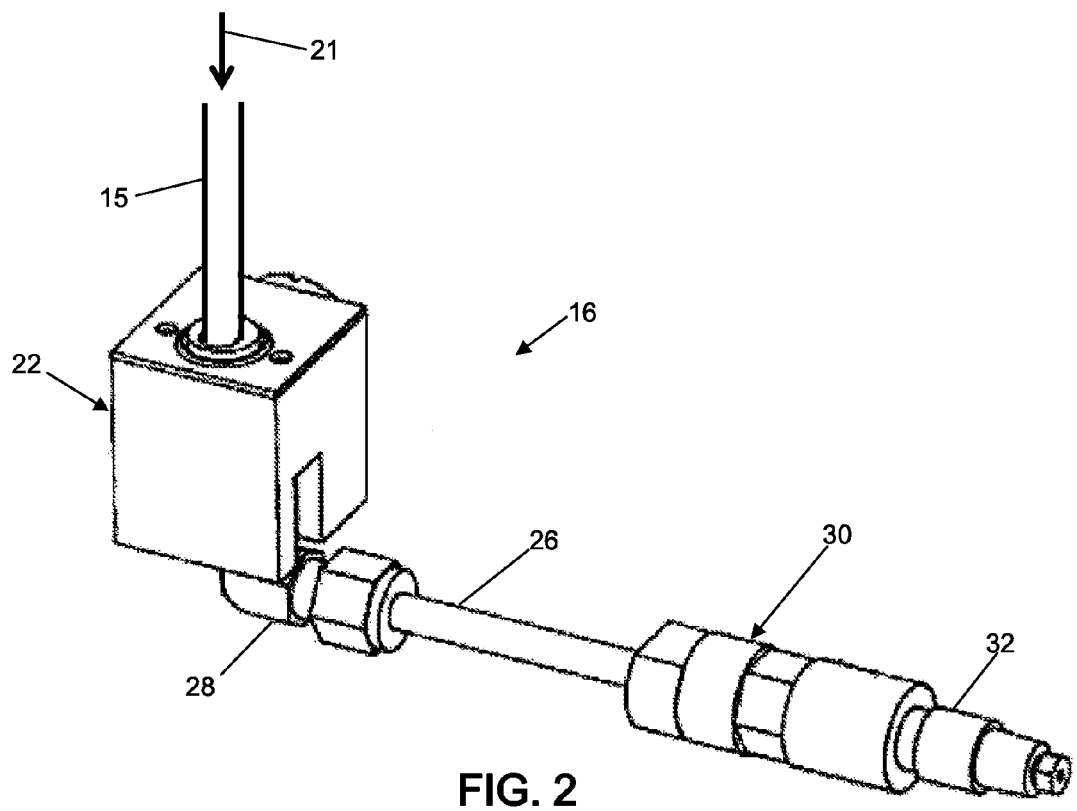
FIG. 2 is a perspective view of a pressure reducer assembly in a first embodiment of the invention.

Referring to FIG. 2, the waste trap assembly 16 is depicted in greater detail in an embodiment of the invention. The waste trap assembly 16 may include a filter assembly 22 having a fluid inlet port 24 operatively coupled to the nebulizer 11 is depicted. The filter assembly 22 may be operatively coupled to a conveyance tube 26 through an elbow 28. A pressure reducer 30 may be in fluid communication with the conveyance tube 26. The pressure reducer 30 terminates at a connection port 32, which is in fluid communication with the container 17. Alternatively, the connection port 32 may be in fluid communication with a drain (not depicted).

Figure 3:
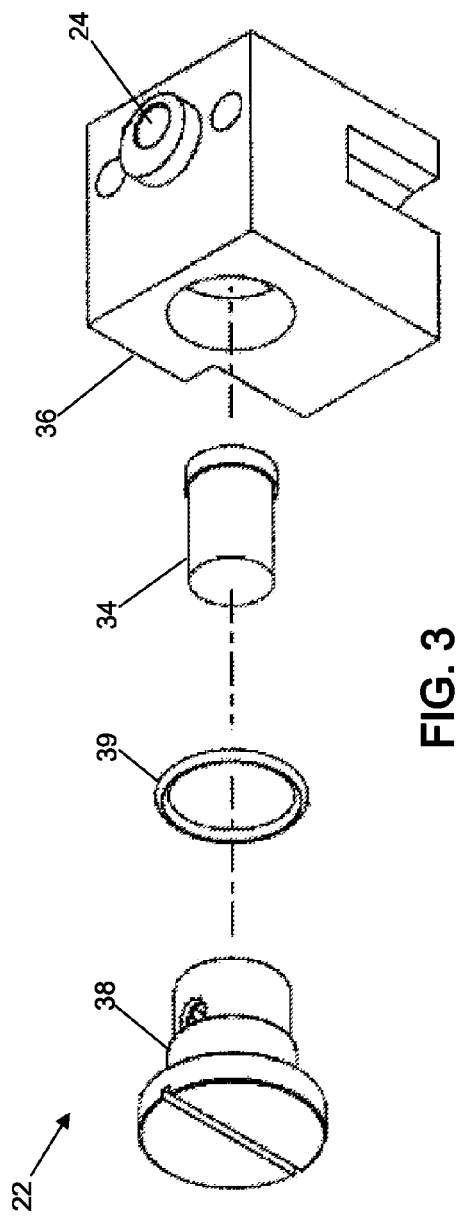
FIG. 3 is an exploded view of the filter assembly of FIG. 2.

Referring to FIG. 3, the filter assembly 22 for use with waste trap assembly 16 is depicted according to one embodiment of the present invention. An inlet port 24 for fluid communication with the waste outlet 15 of the nebulizer 11 is provided on a filter housing 36. A filtering element 34 is secured within the filter housing 36 by a filter access screw 38 sealed with an o-ring 39. In one embodiment of the present invention, the filtering element 34 may be an commonly available inline filter. In other embodiments, the filtering element 34 may be any filter capable of preventing minute solids from clogging the flow restrictors 52 and 54. It is further contemplated that the filtering element 34 may be incorporated within the same housing as the pressure reducer 30.

Figure 4:
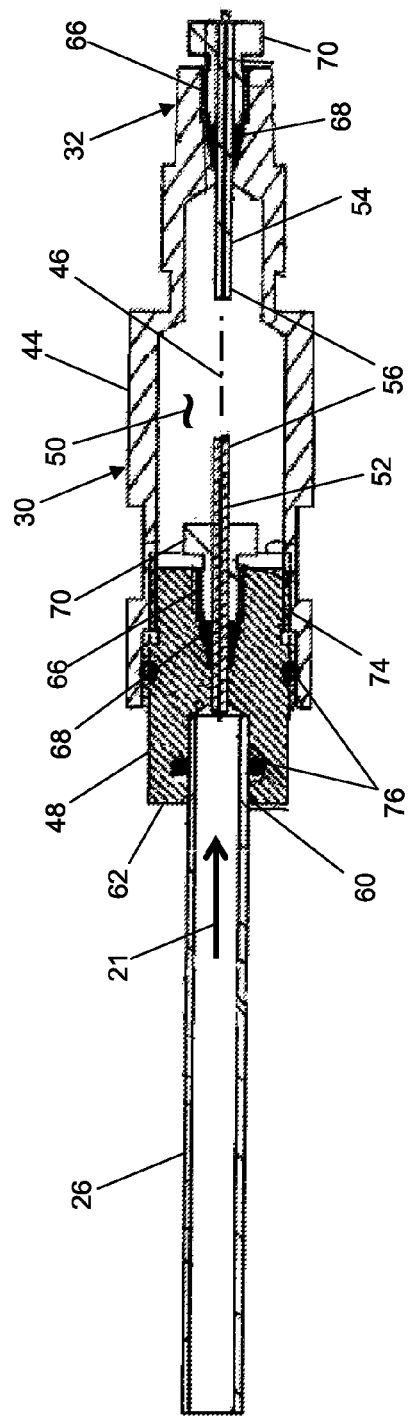
FIG. 4 is a sectional view of the pressure reducer assembly of FIG. 2.

Referring to FIG. 4, the pressure reducer 30, located downstream of the filtering element 34, is depicted in greater detail in an embodiment of the invention. In this embodiment, the pressure reducer 30 comprises a housing 44 that defines a central axis 46 and which cooperates with an end plug 48 to define a chamber 50. A pair of flow restrictors 52 and 54, one located within the end plug 48 and the other within the connection port 42 of the pressure reducer 30, may be substantially aligned along the central axis 46 of the housing 44. The flow restrictors 52 and 54 establish fluid communication between the chamber 50, the conveyance tube 26 and the communication port 32. The flow restrictors 52, 54 may comprise capillary tubes 56 having a large length-to-diameter (L/D) ratio (as depicted) and/or other flow restriction mechanisms such as orifice plates (not depicted).

The end plug 48 optionally includes an inlet port 60 on a proximal end 62 that accommodates the conveyance tube 26. One or each of the end plug 48 and connection port 32 may also define a tapered cavity 66 that accommodates a ferrule 68 and a threaded ferrule fitting 70 for securing the respective capillary tube 56 housed therein and to provide a seal between the capillary tube 56 and the tapered cavity 66. The housing 44 and end plug 48 may include threads 74 for threadable engagement with each other. The pressure reducer 30 may include various o-rings 76 to maintain fluid-tight seals between the various components.

Figure 5:
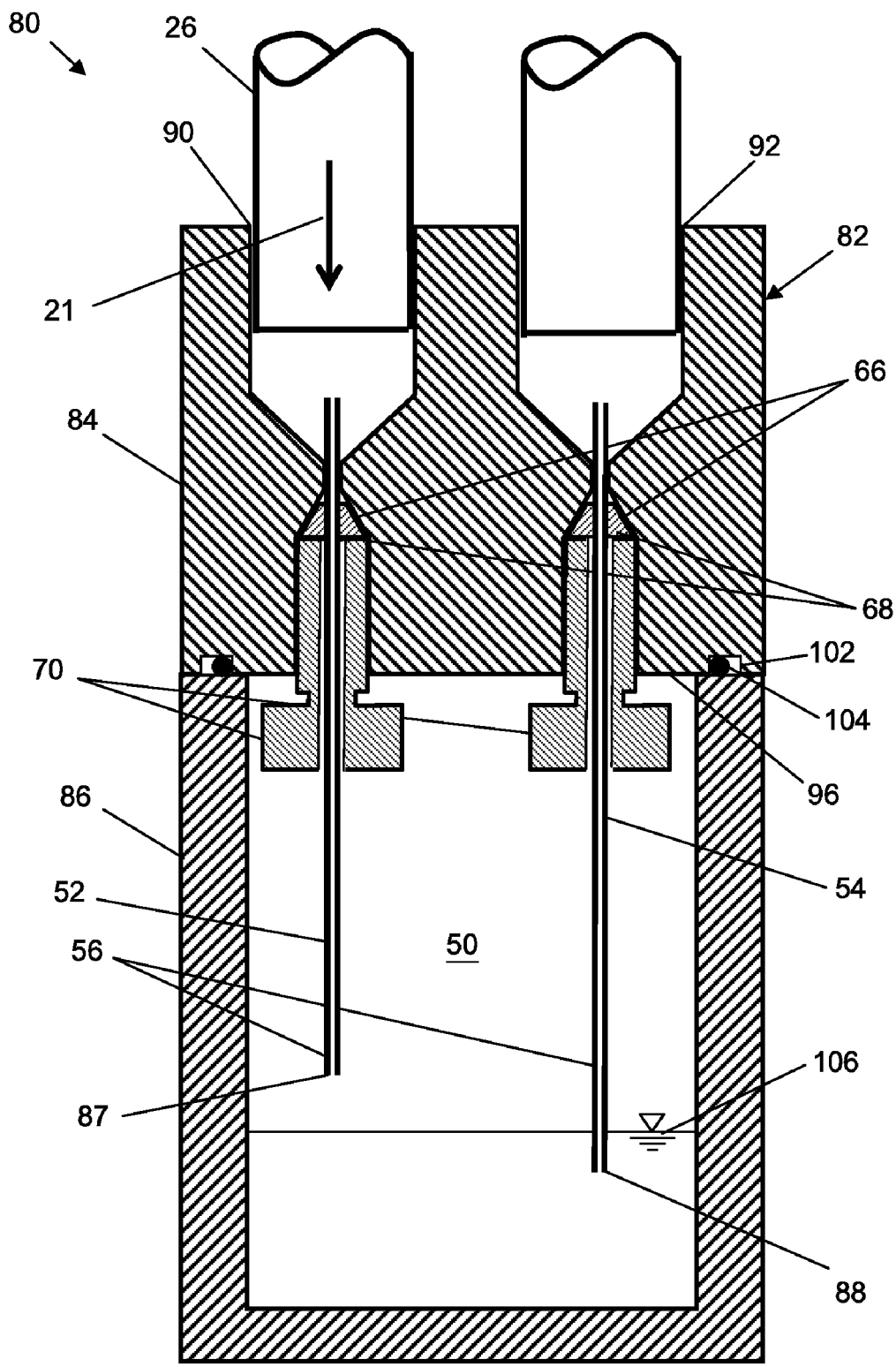
FIG. 5 is a sectional view of a pressure reducer assembly in a second embodiment of the invention.
Figure 6:
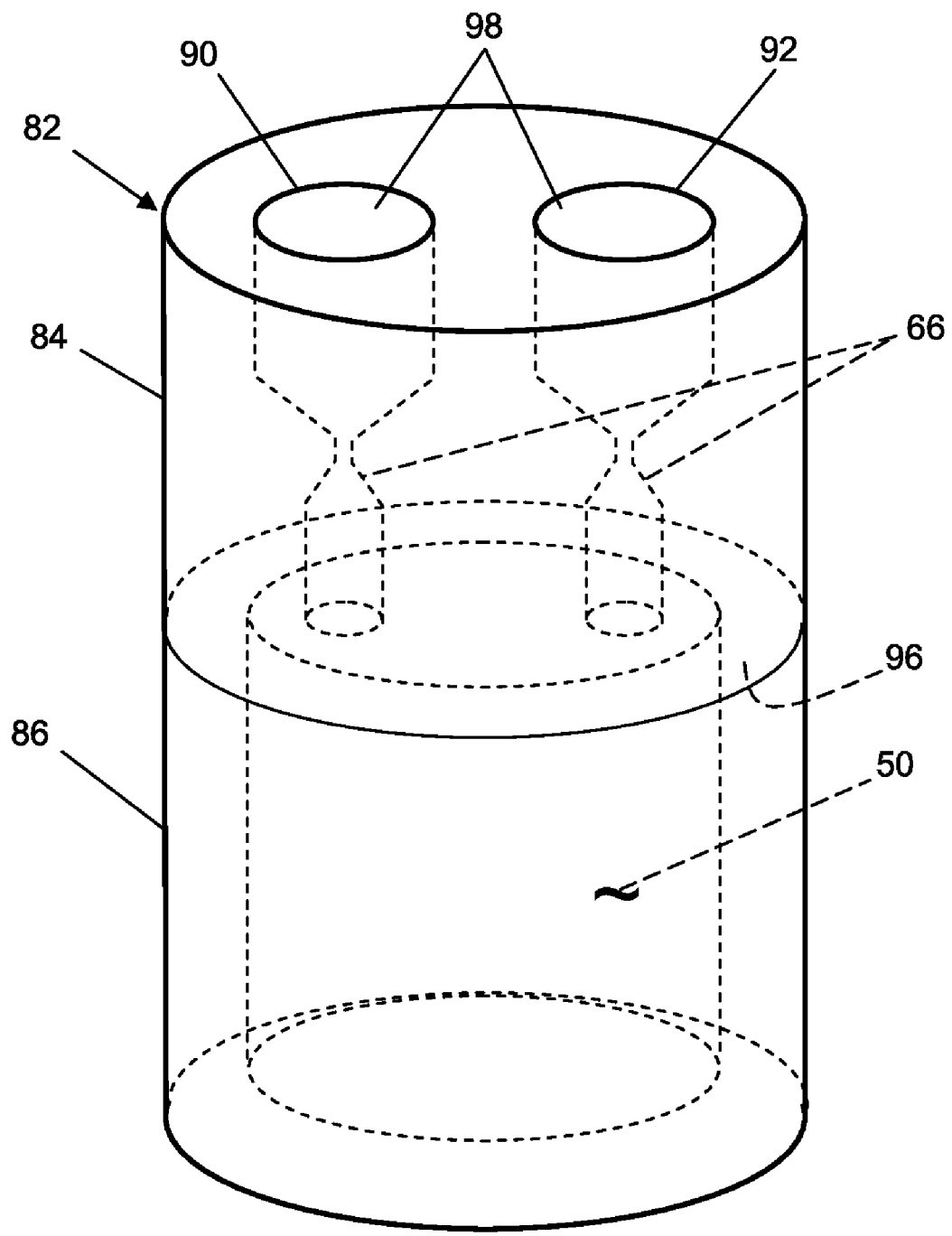
FIG. 6 is a perspective view of the housing of the pressure reducer assembly of FIG. 5.

Referring to FIGS. 5 and 6, a pressure reducer assembly 80 and accompanying housing 82 is depicted in an embodiment of the invention. The housing 82 comprises a top portion 84 and a bottom portion 86 that cooperate to define the chamber 50. (The pressure reducer 80 shares several of the same components and features that perform the same functions as with the pressure reducer 30, which are designated by the same numerical references.) The top portion 84 is configured to house the flow restrictors 52 and 54 such as the capillary tubes 56. Where capillary tubes 56 are utilized for the flow restrictors 52 and 54, the first or inlet flow restrictor 52 may be characterized as having a distal end 87 and the second or outlet flow restrictor 54 as having a proximal end 88 ("distal" and "proximal" being in relation to the direction of flow of the waste stream 21). The proximal end 88 of the outlet flow restrictor 54 may extend further into the chamber 50 than the distal end 87 of the inlet flow restrictor 52, as depicted in FIG. 5.

In one embodiment, the top portion 84 of the pressure reducer 80 includes an inlet port 90 and an outlet port 92 that each pass through the thickness of the top portion 84. Each of the inlet and outlet ports 90 and 92 may be configured with the tapered cavities 66 at one end (depicted in FIGS. 5 and 6 as accessible from an interior or bottom face 96 of the top portion 84) to accommodate the ferrules 68 and the threaded ferrule fittings 70. Accordingly, the capillary tubes 56 of the embodiment depicted in FIG. 5 are secured in place by the ferrules 68 and the threaded ferrule fittings 70 in a manner similar to the pressure reducer 30 of FIG. 3.

The ends of the inlet and outlet ports 90 and 92 that are opposite the tapered cavities 66 (depicted in FIG. 5 as exterior openings 98) may be threaded for coupling to exterior lines (e.g., the conveyance tube 26), and may include o-ring glands (not depicted) for pressure tight seals. Alternatively, openings 98 may be sized for sweat fittings. An o-ring gland 102 and o-ring 104 may be disposed at the interface of the top and bottom portions 84 and 86 (the gland 102 being depicted as formed in the upper portion 84) for fluid containment within the chamber 50. The top portion 84 may be affixed to the bottom portion 86 with fasteners (not depicted), by threadably engaging with each other (not depicted), with detents (not depicted) or by other means available to the artisan.

In operation, the waste stream 21 enters the pressure reducer 30 or 80 via the conveyance tube 26, passes through the first or inlet flow restrictor 52 and enters the chamber 50. As described above, fluid enters the waste trap system 16 at an elevated pressure. The waste stream 21 typically comprises a mixture of fluid and gas, with solids suspended in the liquid. Any suspended solids larger than the internal diameter of the waste trap capillaries are filtered out of the waste mixture by filtering element 34. The filtered waste stream 21 then proceeds through elbow 28 into the conveyance tube 26 where the waste stream 21 is directed into the first or inlet flow restrictor 52.

The waste stream 21 travels through inlet flow restrictor 52 primarily due to the pressure differential between the pressurized waste stream 21 in inlet 26 and the chamber 50. Friction losses through inlet flow restrictor 52 result in a decrease in the pressure head of the waste stream 21. Also, as the waste stream 21 exits the inlet flow restrictor 52 and enters the chamber 50, there is a transition loss in pressure. The chamber 50 fills with waste fluid until it reaches the opening of outlet flow restrictor 54. The waste stream 21 is then pushed through outlet flow restrictor 54, where it is conveyed to the container 17. The damping effect of the chamber 50 in conjunction with the flow restrictors 52 and 54 mitigates the pressure spikes responsible for detection signal noise.

Where capillary tubes 56 are implemented, the waste stream may tend toward discrete, serial plugs of liquid substantially separated by intervals of gas. Liquid that is present in the waste stream 21 collects within the chamber 50 while the gas within the waste stream 21 vents through the second or outlet flow restrictor 54. As the liquid level rises within the chamber 50, the liquid enters the second flow restrictor 54 and passes therethrough in a manner similar to the passage through first flow restrictor 52.

In one example and non-limiting embodiment, the capillary tubes 56 have an internal diameter on the order of 0.25-mm (approximately 0.01-in.) with a length on the order of 25-mm (approximately 1-in.) to provide an L/D ratio on the order of 100. This example configuration was found suitable for reducing a flow stream entering at 3.5-psid to ambient pressure while accommodating flow rates of up to 2.5-ml/min. The inner diameter of approximately 0.01-in. was found to be of sufficient size so as not to clog due to particles present in the waste stream of a CARONA CAD nebulizer. Other dimensional combinations of inner diameter and length of the capillary tubes 56 may be utilized depending on various aspects of a given application (e.g., viscosity of the fluids, size of flow stream contaminants). The capillary tubes 56 may be constructed of PEEK, stainless steel or other materials known in the art to be suitable for the given application. The ferrules 68 may be, for example, a #SS-303-1 stainless steel ferrule such as commonly available from The Swagelok Company of Solon, Ohio, USA. The ferrule fitting 70 may be, for example, a U-311x threaded stainless steel fitting commonly available from Upchurch Scientific, Inc. of Oak Harbor, Wash., USA.

Functionally, waste trap assembly 16 may be designed to create a specific drop in pressure depending on the output of the nebulizer. For pressure reducer assemblies 30 or 80 employing capillary tubes 56, the pressure drop of the flow stream as the fluid travels through the pressure reducer assembly 30 or 80 is governed in part by the ratio of the length to diameter or L/D ratio over the cumulative length of the capillary tubes. For systems with high pressure outputs, the length and diameter of the capillary tubes 56 may be different than a low pressure system. For the pressure reducer assembly 80, the vertical orientation of the outlet flow restrictor 54 generates an additional pressure drop due to the hydrostatic pressure of the column height.

Also, for embodiments having an outlet flow restrictor 54 that extends further into the chamber 50 than the inlet flow restrictor 52, liquid levels such as depicted at numerical reference 106 may tend to be dwell substantially below the distal end 87 of the inlet flow restrictor 52. Such an arrangement can prevent or reduce the amount of liquid that is drawn back into the inlet flow restrictor 52 upon loss of operating pressure in the chamber 50.

In the example configuration described above, the inlet and outlet flow restrictors 52 and 54 comprise the capillary tubes 56, each having a length of approximately 25-mm and an inner diameter of approximately 0.25-mm for an L/D of approximately 100 each or a cumulative L/D of approximately 200. The pressure drop realized for a given L/D ratio vented to atmosphere typically varies with inlet pressure. Accordingly, the cumulative L/D ratio of the capillary tubes 56 may vary, with higher inlet pressures commanding a larger L/D ratio to accomplish the desired pressure reduction to atmospheric pressure.

The sizing of the various components of the waste trap assembly 16 may be difficult to predict due to the intermittent presence of liquid in the inlet and outlet flow restrictors 52 and 54. The equations governing the pressure drop of a laminar flow stream through a tube is given by $$Q = \pi \cdot \Delta P \cdot D^4 / (128 \cdot \mu \cdot L)$$
$$\Rightarrow L = \pi \cdot \Delta P \cdot D^4 / (128 \cdot \mu \cdot Q) \quad \text{Eq. (1)}$$

where Q≡volumetric flow rate (cm$^3$/sec)
L≡length of the tube (cm)
ΔP≡pressure drop along length L of tube (Pa)
D≡inner diameter of tube (cm)
μ≡dynamic viscosity of the fluid passing through the tube (Pa·sec)
The units in parentheses are intended as examples only and are not to be construed as limiting.

As a first approximation, it may be assumed that the flow rate is a combination of the water and air being discharged from the nebulizer. Knowing the approximate flow rates of liquid and gas that enter the nebulizer 11 and the gas that is passed on to the collector 13, one can approximate the liquid and gas flow rates that exit the waste outlet 15 of the nebulizer 11. For example, assuming the flow stream comprises water from the nebulizer that flows at a rate Q of approximately 2.7-cc/min and air from the nebulizer that flows a rate of approximately 150-cc/min, and assuming that the total pressure drop ΔP is 3.5-psid through two capillary tubes in series having an inner diameter of 0.01-in. and of equal length, the estimated length L that will reduce the pressure of the flow stream by the total pressure drop of 3.5-psid is approximately 1.09-in.

The final size of the components may be arrived at experimentally. For example, a pressure reducer having capillary tubes 56 sized above may produce a greater pressure drop than predicted because the minor loss effects are not accounted for in Eq. 1. Accordingly, the capillary tubes 56 may be then trimmed or cut to a shorter length after experimentation to arrive at a desired pressure drop and flow rate combination. The L/D may also be adjusted by substituting in capillary tubes 56 of longer length and/or different diameters.

The chamber 50 may act as a surge suppressor or damper that evens out the alternating plugs of gas and liquid in the flow, thereby reducing pressure spikes. In addition, the pressure reducers 30 and 80 depicted herein include minor losses comprising sharp or sudden flow transitions between the inlet 26 and the inlet flow restrictor 54, the inlet flow restrictor 54 and the chamber 50, the chamber 50 and the outlet tube 54, and between the exit of the outlet flow restrictor 54 and the ambient atmosphere. These sharp flow transitions cause minor losses in caused by the sudden expansions/contractions to the flow stream further add to the pressure drop.

The so-called "minor" losses are described in classical fluid dynamics textbooks such as Fox & McDonald, *Introduction to Fluid Mechanics*, $2^{nd}$. Ed., pp. 368-371 (J. Wiley and Sons, 1978), the specific pages of which are hereby incorporated by reference except for explicit definitions contained therein. In truth, the minor losses can account for the bulk of the pressure losses in a system. Accordingly, alternative embodiments of waste trap systems are anticipated that implement numerous serial chambers connected by orifices and/or tube segments designed to introduce substantial minor losses.

While the depicted embodiments show the flow restrictors 52 and 54 as being in an in-line orientation (FIG. 3) and a parallel orientation (FIG. 5) with respect to each other, it is understood that their orientation relative to each other is not limited in this way. For example, the housing 44 of the pressure reducer assembly 30 may define an elbow shape, so that the flow restrictors 52 and 54 define axes of flow that are perpendicular to each other. Likewise, the inlet port 90 or outlet port 92 of the pressure reducer assembly 80 may be located on the side of the top portion 84 so that the flow restrictors 52 and 54 define axes of flow that are perpendicular to each other. The pressure reducer assembly 30 may also define an inlet and outlet that are eccentric with respect to each other so that axes of flow of the flow restrictors 52 and 54 are substantially parallel but not in line; such a configuration could be used so that the second or outlet flow restrictor 54 starts to drain the chamber 50 before the liquid level reaches the height of the first or inlet flow restrictor 52.

Each of the embodiments depicted herein present only a single chamber 50. It is understood that more than one chamber can also be employed and still in accordance with the spirit of the invention. For example, a pressure reducing system could include capillary tubes for the inlet and outlet, with several chambers therebetween, the chambers being separated by and in fluid communication with each other through orifice plates. Multiple chambers would thus provide the advantage of multiple mechanisms for minor losses.

The foregoing descriptions present numerous specific details that provide a thorough understanding of various embodiments of the present invention. It will be apparent to one skilled in the art that various embodiments, having been disclosed herein, may be practiced without some or all of these specific details. In other instances, known components have not been described in detail in order to avoid unnecessarily obscuring the present invention. It is to be understood that even though numerous characteristics and advantages of various embodiments are set forth in the foregoing description, together with details of the structure and function of various embodiments, this disclosure is illustrative only. Other embodiments may be constructed that nevertheless employ the principles and spirit of the present invention, which is defined solely by the claims that follow.

For purposes of interpreting the claims for the present invention, it is expressly intended that the provisions of Section 112, sixth paragraph of 35 U.S.C. are not to be invoked with respect to a given claim unless the specific terms "means for" or "step for" are recited in that claim.

What is claimed is:

1. An apparatus for reducing the pressure of a fluid flow stream, comprising:
   a pressure reducer assembly defining a chamber therein, the pressure reducer assembly further comprising:
      a first flow restrictor configured to receive said fluid flow stream and to deposit said fluid flow stream into said chamber, said first flow restrictor defining a first flow axis and being tailored to cause a predetermined first reduction in pressure; and
      a second flow restrictor configured to receive said fluid flow stream from said chamber and to convey said fluid flow stream out of said chamber, said second flow restrictor defining a second flow axis and being tailored to cause a predetermined second reduction in pressure,
   wherein at least one of said first and second flow restrictors comprises a tube having a length and an inner diameter,
   wherein said fluid flow stream exits said second flow restrictor at substantially atmospheric pressure.

2. The apparatus of claim 1 further comprising a filter located upstream of said first flow restrictor.

3. The apparatus of claim 1 wherein said tube of said at least one of said first and second flow restrictors is oriented substantially vertically.

4. The apparatus of claim 1 wherein said first and second axes of flow are substantially parallel.

5. The apparatus of claim 4 wherein said first and second axes of flow are substantially co-linear.

6. The apparatus of claim 1, wherein said pressure reducer assembly is operatively coupled with a waste stream of a High Performance Liquid Chromatography system.

7. A method for reducing the pressure in a waste receptacle comprising:
   providing a first flow restrictor in fluid communication with a chamber and a second flow restrictor in fluid communication with said chamber and said waste receptacle, at least one of said first flow restrictor and said second flow restrictor including a tube having a length and an inner diameter;
   causing a fluid that is at a first pressure to flow through said first flow restrictor, said first flow restrictor being configured to create a first loss of pressure when said fluid enters said first flow restrictor at said first pressure, said first pressure being greater than atmospheric pressure;
   causing said fluid that flows through said first restrictor to flow into said chamber, said chamber operating at a second pressure that is greater than atmospheric pressure and less that said first pressure;
   causing said fluid that is at said second pressure to flow through said second flow restrictor, said second flow restrictor being configured to create a second loss of pressure when said fluid enters said second flow restrictor at said second pressure; and
   causing said fluid that flows through said second flow restrictor to flow into said waste receptacle, said waste receptacle being substantially at atmospheric pressure.

* * * * *